(12) United States Patent
Stoppelbein et al.

(10) Patent No.: US 9,724,424 B2
(45) Date of Patent: Aug. 8, 2017

(54) MAGNETIC ACOUSTIC RESONANCE LIGHT AND HOMEOPATHIC THERAPY CRYSTAL

(71) Applicants: DeCauter Ward Stoppelbein, Cool, CA (US); Carly Ann Babb, Cool, CA (US)

(72) Inventors: DeCauter Ward Stoppelbein, Cool, CA (US); Carly Ann Babb, Cool, CA (US)

(*) Notice: Subject to any disclaimer, the term of this patent is extended or adjusted under 35 U.S.C. 154(b) by 437 days.

(21) Appl. No.: 13/839,983

(22) Filed: Mar. 15, 2013

(65) Prior Publication Data

US 2014/0271556 A1    Sep. 18, 2014

(51) Int. Cl.
C30B 29/00    (2006.01)
A61K 47/46   (2006.01)
A61K 33/00   (2006.01)

(52) U.S. Cl.
CPC ............. *A61K 47/46* (2013.01); *A61K 33/00* (2013.01)

(58) Field of Classification Search
CPC ................................ C30B 29/00; C30B 30/04
See application file for complete search history.

(56) References Cited

U.S. PATENT DOCUMENTS

2012/0272583 A1* 11/2012 Frushour .................. B01J 3/062
51/309

OTHER PUBLICATIONS

Thomas R. Firor, MD, Homopathy and Electromagnetic Devices, 2004, pp. 1-4, Part 1.
Dino Deghionno et al., Tucson '97, Gem N.E.W.S, 1997, pp. 60-70, vol. 33, No. 1.
Si & Ann Frazier, The Very Essance, Lapidary Journal, 1993, Lapidary Journal Inc., California.
David Alexander, Can you compress a liquid (water)?, 1, Dec. 20, 2001, Physlink.com, internet at http://web.archive.org/web/20011220190001/http://physlink.com/Education/AskExperts/ae15.cfm.†

(Continued)

*Primary Examiner* — Rosanne Kosson
(74) *Attorney, Agent, or Firm* — Mohr Intellectual Property Law Solutions, PC

(57) ABSTRACT

A quartz or otherwise similar crystal ('host crystal') embedded with minerals, metals, homeopathic, organic/inorganic, and magnetic materials (which allow for magnetic interactions) and the method for embedded 'host crystal' with said materials is disclosed. The 'host crystal' can be any size, shape, cut, or color of crystal. A hole/depression is first drilled/etched anywhere on the quartz or similar 'host crystal', this hole is then filled with a chosen combination of materials using force/compression, and are semi-permanently sealed by compressing metal flake or powder onto/into the top of the material-filled hole in the 'host crystal'. The compression of the materials inside of the 'host crystal' increases the natural piezoelectric, ionic emission, magnetic field, and vibrational properties/emissions, allows for magnetic interactions, increases their scientific and potential therapeutic effects, and has applications for decorative specimens, energy healing/homeopathic/vibrational therapies, water energizing/structuring, and is most often incorporated into gem, mineral, magnetic, and homeopathic light therapies.

18 Claims, 4 Drawing Sheets

(56) References Cited

OTHER PUBLICATIONS

Pathan Salman et al, Why can't liquids be compressed?, 4, Aug. 29, 2012, Quora, internet at http://www.quora.com/Why-cant-liquids-be-compressed.†

Matthew Zelisko & Kimberly Anderson, Lesson: Piezoelectricity, 8, Oct. 2014, Teachengineering.org, internet at https://www.teachengineering.org/view_lesson.php?url=collection/uoh_/lessons/uoh_piezo/uoh_piezo_lesson01.xml.†

Satya Center, Crystal Gallery, 7, Oct. 13, 2010, Satya Center, internet at http://web.archive.org/web/20101013013344/http://www.satyacenter.com/store/crystal/collectors_corner.†

Applicants, Vogel Crystals and Apollo Vogel Crystals, 4, Jun. 29, 2011, Treeofllifetech.com on youtube, internet at https://www.youtube.com/watch?v=kCGioQYL5hs.†

Applicants, Welcome to Tree of Life Technologies, 37, Dec. 31, 2010 & Feb. 8, 2011, treeoflifetech.com, internet at http://web.archive.org/web/20101231014937/http://treeoflifetech.com/.†

Duncan Pay, Innovative Optical Effects, Unique rings with raw crystals, Tucson 2014, 3, Gemological institute of America, internet at http://www.gia.edu/gems-gemology/spring-2014-gemnews-tucson-unique-rings-optical-effects.†

Bubbles, Using Crystals, Magnets and Sacred Geometry, 2, Jul. 21, 2011, Lightworkers, internet at http://lightworkers.org/blog/136864/using-crystals-magnets-and-sacred-geometry.†

Crystalline Power Pouch, Empowerment33, 1, Jun. 15, 2011, empowerment33.com, internet at http://web.archive.org/web/20110615060824/http://www.empowerment33.com/.†

\* cited by examiner
† cited by third party

MAGNETIC ACOUSTIC RESONANCE LIGHT AND HOMEOPATHIC THERAPY CRYSTAL

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

Field of the Invention

The present invention is in the technical field crystallography. More particularly, the present invention is in the technical fields of crystallography, homeopathy, vibrational and magnetic therapy and enhancements.

More particularly, the present invention directed to the fields of holistic health-care, light therapies, Homeopathic, and magnetic 'energy' therapy/enhancement devices.

This invention is a mineral filled, metallically filled, homeopathically filled, magnetically compressed/driven quartz (or similar) crystal. This invention is be used as a magnetic, homeopathic, vibrational, and light therapy/enhancement, as well as having applications as jewelry/keepsake magnetic and homeopathic adornment or enhancement/therapy devices.

Magnetic therapies are becoming a very common health treatment/supplement/enhancement, and some forms of magnetic therapy have achieved limited FDA approval for the effectiveness of magnets in pain management and other areas of western healthcare. Further, many traditional, alternative, and holistic health care providers, are utilizing quartz crystals and various other gems and minerals as "vibrational", "energy", and "Homeopathic" therapies. Quartz as well as other minerals has proven scientific effects on electromagnetic fields, and specific frequencies that come into contact with the particular mineral. Gems and minerals have their own vibrational and electromagnetic frequency emissions, as well as emitting negative ions, and having various vibrational interactions that are seen by some healthcare practitioners and many people worldwide to have beneficial to effects to both health and state of mind. Magnetic, crystal/gem, homeopathic, and mineral therapies are effectively combined in this invention to allow for wider variety of uses in potential enhancements, treatments/therapies.

This invention will be used as homeopathic magnetic therapy jewelry/adornment and various other decorative uses of this technology. This invention is also used in holistic-homeopathic energy therapies such as Reiki, as well as in vibrational/resonance therapies such as sound therapy. This invention will be used as a magnetic field therapy/enhancement and thereby has applications in the energizing/magnetizing or "structuring" of water. This invention is often used in combination with various sources of light, making this invention a 'magnetic mineral/gem light therapy.' This invention has applications as keepsakes, jewelry, adornment, and homeopathic decoration. As well as having therapeutic and scientific application as magnetic therapies/enhancements, homeopathic therapies/enhancements, vibrational therapies/enhancements, energy therapy/enhancement, and light therapy/enhancement.

Until this present invention, therapy devices of magnetism have been largely separated from other holistic and homeopathic materials used commonly in holistic therapies. Items such as crystals/gems, minerals, homeopathic remedies, and light therapies, have largely required separate devices and thereby separate treatments. Furthermore, other devices and therefore other magnetic field, light, homeopathic and holistic materials/treatments have not been combined in a way that allows for an infinite variety of gems, minerals, homeopathic, precious metals, and materials that are deemed beneficial to the body and/or the energy fields related to the body, to be used together in any way. Further, many people are turning to pendants and jewelry that contain the many of the individual materials that compose this invention, as a way to enhance their blood-work and/or bio-energetic systems. With applications in jewelry and decorations, this invention incorporates materials and energies used in magnetic, homeopathic, vibrational, energy, light therapies and enhancement, this invention allowing for infinite varieties of holistic materials to be used in a way that is both aesthetic and holistically beneficial/enhancing.

Further, unique optical effects provide by and created by interacting light with the material combinations of this invention provide for unique optical effects and characteristics that give this invention unique properties for various light therapies.

DESCRIPTION OF THE RELATED OR PRIOR ART

Crystal, mineral, gem, homeopathic, and magnetic materials have not been combined in this way before this invention. The Prior art pertaining to drilling and filling quartz crystals with any of them materials (which are listed in the 'detailed description' of this application) consists of a quartz crystal cut to resemble a carrot-shape called a Pranic-cut of quartz crystal. That cut quartz crystal is drilled and the resulting hole is filled with a single rod of gold. This is known as a "gold-rod Pranic crystal", and is used by the Pranic Healing association as an 'energy healing' tool. That tool does not use or combine any other materials or any other metals besides a single gold rod inserted into the larger end of the carrot-shaped quartz crystal. To our research, there has been no compression of gems, minerals, magnetic materials, homeopathic materials, keep-sake materials, or any of the other materials described in this invention, into the inside of any quartz, gem, or any synthetic crystal material. The Pranic Healing Association does not use compression on their gold rods; they are slid into place inside of the crystal with no true compression.

There is no prior art regarding the magnetic compression or placement of magnets/magnetism into the inside of a crystal, and more over there is no prior art of the magnetic interactions driven inside of the crystal through the interaction of magnets and minerals as in this invention. There prior art for the magnetic interactions within, and the magnetic compression of the quartz through its being filled with iron and other magnetically conductive materials inserted into the quartz, and then magnetized with magnets or electromagnetism.

There is no prior art regarding the setting of minerals, metals, homeopathic materials, plant materials, medicinal or vitamin materials into quartz, nor any of the other ingredients that are listed in this patent application. Nor is there prior art regarding the capping of these stated materials into any crystal with precious metals or glues/epoxies.

The prior art pertaining to 'gem light therapy' are a variety of therapies using anywhere from 1, to about 12 solitary/separate cut and faceted gems or crystals with light being shone through them. There is also a quartz light therapy involving 1-12 solitary quartz crystals. This is known as crystal light therapy. There is no magnetism involved in those therapies as in this invention, nor is there any of the metals, vitamins, herbs, medicinal, and homeopathic materials involved in prior art regarding 'gem light therapies'. Nor do those therapies involve the variety or number of gem species that this invention consists of.

SUMMARY OF THE INVENTION

Note: The basis quartz (or similar) crystal that will be filled and magnetized in this invention will be referred to as the 'host' and/or 'host crystal' in and throughout this patent application.

The present invention is a quartz, crystal, gem, mineral, homeopathic, and magnetic therapy device. A way of combining and compressing quartz (and similar types of) 'host' crystals; with magnetism, precious and non precious metals, minerals, gems, plant materials, homeopathic remedies, homeopathic waters, and other materials to be described/detailed later in the detailed description. Any quartz or similar crystal is drilled, and then filled with a variety of these materials. Then magnets can be added to that filled quartz or similar 'host crystal' that compress the 'host crystal' by the magnetic interactions created. The materials added to the 'host crystal' are compressed into the 'host crystal' and the magnets are used to interact magnetically with these fillings into the 'host crystal' as well as provide further compression onto quartz (or similar) 'host crystal'. Magnets/magnetism that are seen as beneficial in magnetic therapies will cause compression onto and into to the quartz 'host' crystal and other materials filled into it. The materials themselves, as well as the compression of these materials into the inside of the 'host' quartz (or similar) crystal, as well as the magnetic compression, will enhance the quartz's piezoelectric and ionic emissions, as well as create a magnetic field in, around, and within the 'host crystal' and it's fillings. The fillings themselves can add to the electromagnetic field of the 'host' crystal, and can be piezoelectric as well, creating their own electromagnetic field. There is a measurable ionic, vibrational, and magnetic energy that comes from this magnetic interaction and compressed quartz. This is seen as beneficial to many holistic health-care therapists. The materials added to the inside of the quartz will enhance the quartz's intrinsic, aesthetic and monetary value, and the scientific actions of the magnetic and energetic materials enhance the various material's enhancement/therapeutic effects.

This Invention is Described Here in 2 Parts.

The first part is to add/compress various materials into the inside of a quartz or similar crystal, and to functionally cap those materials into the inside of the quartz.

A quartz or similar crystal is drilled/routed/engraved, and the resulting hole/depression is filled and various holistic materials that are compressed with force into the inside of the quartz (or similar) crystal. The materials that we describe in this part of this application are materials that we are the first to place into a hole inside of quartz or similar crystals, and it is of the primary/fundamental basis of this invention and application. This patent application is for the patent rights to put any of these materials, and any combination of any of these materials inside of holes drilled into quartz or similar 'host crystals'. Again, we are the first to add these materials to the inside of crystalline materials, and we are seeking patent protection rights for this use of any and/or all of these materials.

These materials that are compressed into the inside of quartz (or similar) 'host crystals' consist of:

1. All Gems and Minerals. All crystallographic materials whether they are naturally occurring, man-made, laboratory grown/produced. All Gems and Minerals of both terrestrial and non-terrestrial origins, including meteorites.
2. All Precious and non-precious metals. This application includes metals originating from terrestrial and non-terrestrial origins (with the exemption of the single solid gold rod placement of the 'Pranic crystal' prior art).
3. All materials deemed beneficial by allopathic-western or holistic alternative health care therapists including; vitamins, medicines, herbs, herbal remedies, plant essences, herbal essential oils, vitamin materials, nutriceutical materials, prescription drugs, non-prescription drugs, homeopathic remedies, all 'beneficial' bacteria, cell life such as spirrullina, microbes, all plant materials, monatomic gold (Ormus), Tachyons, Orgone, ceramic materials, infrared ceramics, all monatomic elements.
4. Items of special significance or intrinsic value including; plants, plant materials, animal remains, insects, insect remains, human remains, ashes, souvenir materials, glass, and homeopathic 'healing' water.
5. Magnets and Magnetized materials To reiterate, the first part of this patent is to add varying amounts of these listed materials into a hole, which is drilled into a quartz, calcite, topaz, ruby, sapphire, diamond, tourmaline, or similar gem or crystal.

These descriptions will continue to refer to the crystal that will be filled with these listed materials as the "host" crystal. The 'host crystal' is most often quartz, but can be any crystalline gem or mineral, whether it is natural, synthetic, man-made, or laboratory grown/produced. To clarify: the first part of this invention is to add and compress gems, metals, minerals, plant materials, homeopathic materials, magnets, and varieties of organic and non-organic materials into the inside of any quartz, calcite, tourmaline, sapphire, ruby, topaz, agate, or similar 'host crystal'.

Varying combinations these materials are packed and compressed into the inside of a quartz (or similar) 'host crystal'. These materials are added and packed into a hole that is drilled into, or completely through the 'host crystal'. These materials are compressed into the drilled hole of the 'host crystal' by means of mashing and compressing the materials with a rod type tool. Mechanical compression devices such as a vice-press or a machine press can be used gather and force more compression onto the materials into the quartz. The minerals, metals, gems, and other materials are compressed into the 'host crystal', and then capped into the 'host crystal' with metal. The metal 'capping' is accomplished in this invention by the pressing and mashing of fine metallic flake onto the top of the materials that fill the hole in the 'host crystal'. The mashing of the flake is done until the metal flake becomes a solid metal cap on top the materials inside of the crystal. This effectively and semi-permanently caps the materials into/inside of the 'host crystal'. Through the compression techniques outlined, the metal flake being compressed into a solid piece of metal, and semi-permanently capping the materials into the inside of a 'host crystal'. In this capping process, any metal may used; gold, platinum, silver, copper, brass, and/or other metal flake can be used in their pure forms, or in mixtures/alloys/blends of metal flakes. The process of filling and compressing these materials into the inside of a crystal, as well as capping the 'host crystal's' material into the hole by the compression of powdered metals, are all new processes and new ways of combining these materials. This description of the Drilled, material-filled, Metal-capped 'host crystal' completes part 1 of the summary description this invention.

Part 2 of this summary of this invention entails the adding of magnets to the quartz (or similar) 'host crystal'. This application adds further compression to the surface of the 'host crystal', as well as creates a magnetic field within and around the 'host crystal'. The magnets are to be aligned to interact with the magnetically conductive metals, minerals, and other conductive materials that are filled into the inside of the 'host crystal' described in part 1.

In this, part 2 of this summary describes the bonding of magnets onto the surface of the 'host crystal', or recessing the magnets into the 'host crystal' described in part 1. The semi-permanent or permanent bonding/setting of magnets onto the 'host crystal' is accomplished by gluing, electro-forming, Velcro, or by any other means of bonding/sticking the magnets onto the surface of the 'host crystal'. Magnets can also be set/recessed into a hole that is pre-drilled into the crystal and then glued into place. The recessed magnets in this invention can also be set into a hole and then capped with metal flake. The metal flake is compressed onto the top of the magnets and a solid metal cap is formed, doing so exactly as described prior in this summary. The magnets that are set on or within the 'host crystal' are aligned onto or into the 'host crystal' in patterns and alignments that cause tension and compression onto the surface of the 'host crystal' and also within the 'host crystal' through the magnets' alignments and attractions, and also the attractions created between the magnets and the magnetically conductive filled into the inside of the 'host crystal'.

This compressing of the 'host crystal' is caused by the magnetic forces between the magnets themselves, but is also due to the magnetic interactions with the magnetically conductive materials that are compressed into the inside of the 'host crystal'. These magnets will be aligned in patterns that will allow their magnetism to interact with each other through the crystal. This not only compresses the 'host crystal', but it allows for the continual magnetic interaction between the magnets that are set on the 'host crystal', with the minerals and metals that contain iron and themselves are magnetically conductive and transducers of magnetic energy which have been compressed into the inside of the 'host crystal' as described in part 1. This magnetic interaction cause further compressions and stress to the quartz, compression that will increase the quartz's natural piezoelectric output, this stimulates and energizes certain homeopathic materials and certain other mineral materials inside of the 'host crystal'.

Figure 1:
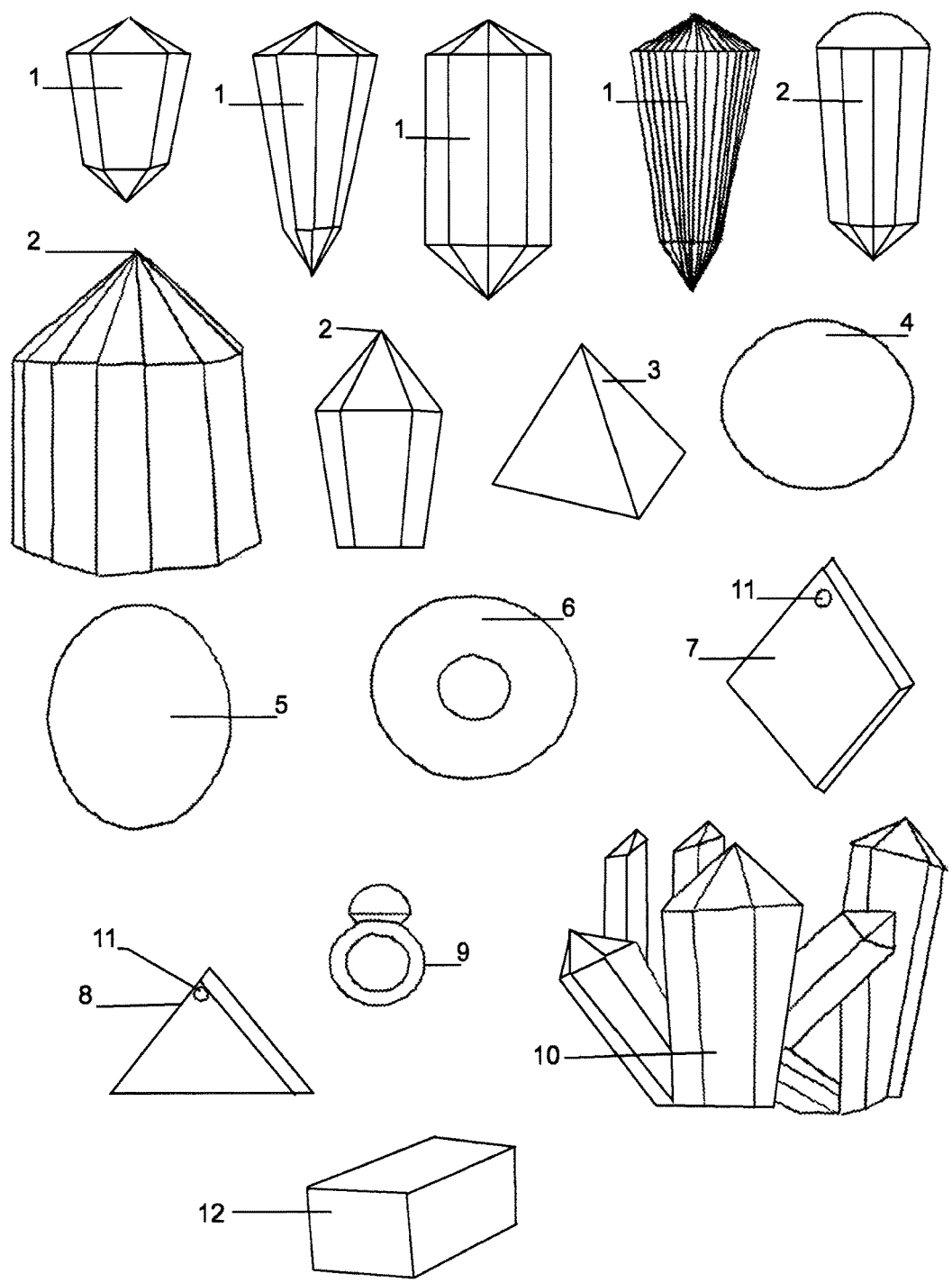
FIG. 1 Drawing:
Common (host) crystal shapes.
This page shows numerous examples of 'host crystal' shapes and styles. The sizes of all of these shapes are irrelevant to their representation as/of 'host crystals'. All shapes and sizes will be used in relatively the same way in this invention.

1. Example of a Vogel style cut crystal. Also known as a double terminated or DT Cut crystal
2. Example of a Single Terminated or Single Pointed crystal Carved-cut or naturally occurring
3. Pyramid shaped crystal
4. Spherical or ball shaped crystal
5. Egg shaped crystal
6. Doughnut shaped crystal
7. Diamond shaped crystal (shown as a pendant with a line representing a necklace)
8. Triangular shaped crystal (shown as a pendant with a line representing a necklace)
9. Crystal mounted on jewelry (shown as a finger-ring)
10. Naturally occurring or manufactured crystal cluster
11. Represents a hole or jewelry setting for a necklace
12. Represents geometrically shaped crystals, shown in this reference as a cubic crystal. This invention entails using any geometrically carved or naturally shaped crystals, including the platonic solids, and all other geometric shapes of crystals.

Note: All of these shapes are used in largely the same way in this invention regardless of actual size, shape, color, clarity, weight, cut, facets, perspective, mass, dimension, etc.

Figure 2:
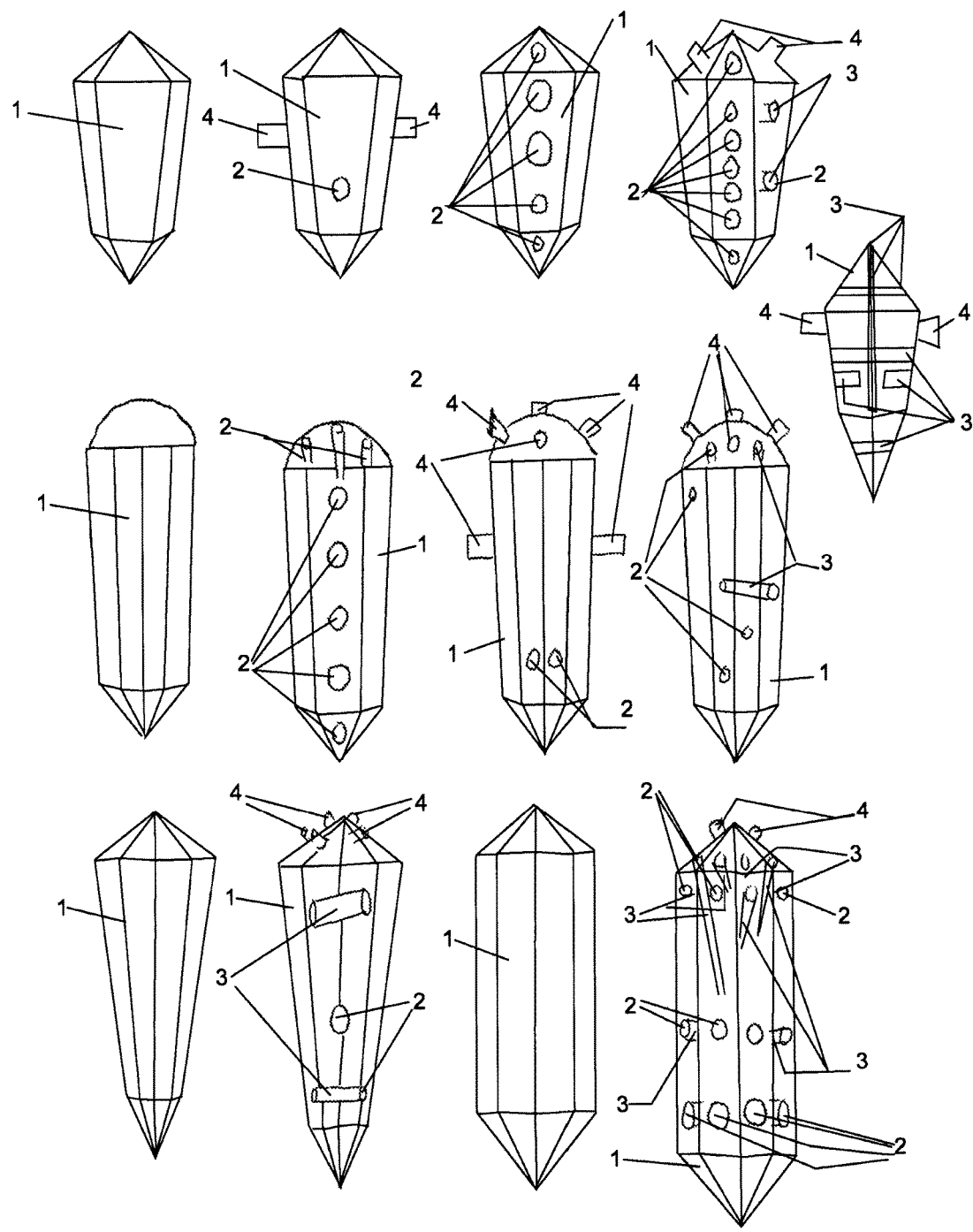

FIG. 2 Drawings:
Vogel style crystals, single and double terminated 'host crystals', shown filled, capped, and with magnets attached.

1 is/are perspective side views of terminated (pointed) crystals in various carved and natural shapes. These crystals are known as "laser points", "Vogel" and "Pranic" crystals, as well as they are double and single terminated/pointed crystals. The crystals of this invention come in all shapes (natural and cut) and all sizes, and are used in largely the same ways. The drawings of the various crystals used in this invention are representative of all crystal shapes and sizes that are used in largely the same in this invention.

1 is numerous examples of crystal shapes. These may be any crystal cut, shape, size, weight, or color, and are the material basis of this present invention.

2 is a perspective view of the metal-caps, which are metallic flake that has been pressed onto/over the mineral filled holes. The circles of 2, cap the holes that are drilled into any part of any crystal of this invention. This hole and cap may be anywhere on the crystal, and drilled to any depth, on any crystal, regardless of shape or size.

3 is a side view of the tunnels/holes, which is drilled into and/or through the crystal. These holes/tunnels of 3, are drilled into the crystal, filled with ingredients described in this invention, and capped with metal as represented as 2

4 is perspective views of magnets, which are glued onto the surface, and/or recessed into the crystal. These magnets entailed and incorporated in this invention can be of any size or shape. The placements shown on the 'host crystal' as well as the perspective sizes are only examples. Magnets can be of any size or shape relative to the 'host crystal', and there is no specific minimal or maximum number of magnets that are used in this invention. The magnets represented in 4 vary in size and shape, and are usually rare-earth neodymium, samarium cobalt, or ferrous magnets, but can consist of any other applicable forms of magnetism including electromagnets.

Figure 3:
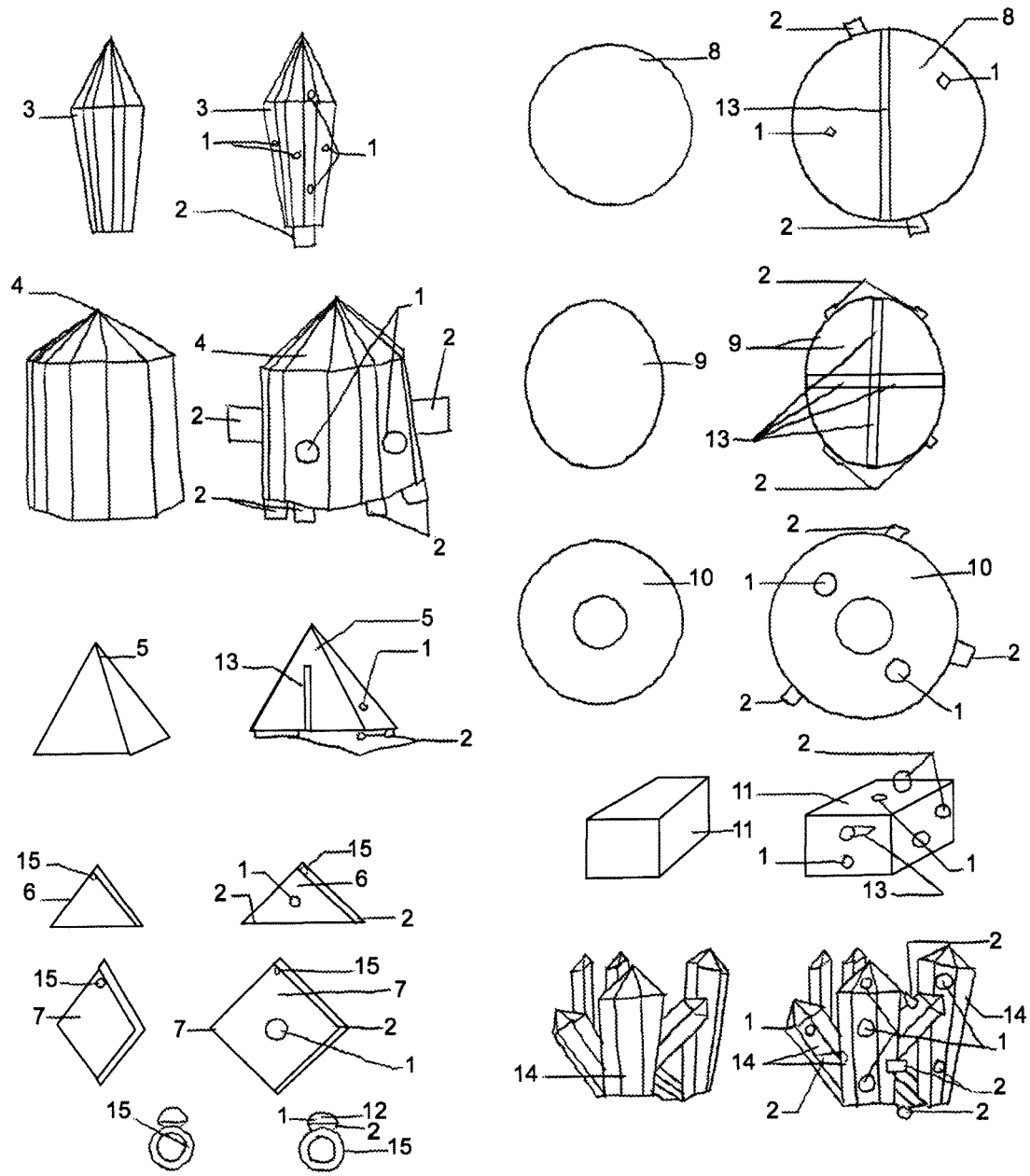

FIG. 3 Drawings:
Flow chart of crystal shapes, metal caps, and magnets.

3 Drawings shows various 'host crystal' shapes from 1, and shows each of these shapes filled, capped, and with magnets added as described in this invention.

1. Represents a metallic cap onto a mineral, gem, organic material, etc. filled hole
2. Represents a magnet that is attached to the surface, or recessed into the surface of the 'host crystal'.
3. Represents a naturally occurring or carved 'host crystal' known as a Single terminated/pointed crystal.
4. Represents a slightly different style of single terminated/pointed 'host crystal'.
5. Represents a 'host crystal' in the shape of a pyramid.
6. Represents a triangular-shaped 'host crystal', a jewelry pendant design of crystal.
7. Represents a diamond-shaped 'host crystal'. Shown here as a jewelry crystal.
8. Represents a ball, sphere, or disk shaped 'host crystal'.
9. Represents an egg or ovular-shaped 'host crystal'.
10. Represents a doughnut-shaped 'host crystal'.
11. Represents a cube-shaped 'host crystal'. Each and every shape or geometry of crystal is used in largely the same manner in this invention.
12. Represents a 'host crystal' on a jewelry ring setting.
13. Represents the holes or tunnels that are drilled into the 'host crystal', these holes are filled with the materials described of this invention.
14. Represents a crystal cluster. A naturally occurring or manufactured 'host crystal' cluster.
15. Represents a hole or jewelry setting for this 'host crystal', in order that it may be used as a jewelry pendant.

FIG. 4 Drawings:

Common shapes of 'host crystals', their caps and magnets.

1. Represents a metallic cap that has been put onto a 'host crystals' drilled and filled hole.
2. Represents the hole/tunnel/chamber that is made into the 'host crystal' by drilling into it.
3. Represents a hole for a jewelry setting or necklace to be used in this 'host crystal'. This is done so that the 'host crystal' can be made into a pendant or other jewelry piece.
4. Represents magnets that are glued or otherwise attached to the surface, or recessed into the 'host crystals.' Magnets may be in any shape or size relative to the 'host crystal' in this invention.
5. Represents a pyramid-shaped crystal.
6. Represents the bottom of the crystal pyramid that is seen in 5.
7. Represents a Single terminated/pointed (S.T.) crystal.
8. Represents another type of Single Terminated Crystal.
9. Represents a crystal sphere, ball, or disk. All shapes are used in the same manners regardless of perspective.
10. Represents an egg or ovular shaped crystal
11. Represents a triangular shaped crystal pendant
12. Represents a doughnut shaped crystal
13. Represents a diamond shaped crystal pendant
14. Represents a crystal jewelry ring
15. Represents a cubed crystal
16. Represents a crystal cluster. Naturally occurring or manufactured.

DETAILED DESCRIPTION OF THE INVENTION

Referring to this invention in greater detail. The basis of this invention is a quartz or similar crystal, and is referred to in this patent application as being the 'host crystal' of this invention. The 'host crystal' of this invention can be of any size, color, shape, mass, weight, cut, design, or type of gem or crystal. This process can be used in any quartz, calcite, tourmaline, selenite, topaz, amethyst, sapphire, agate, ruby, morganite, moldavite, kunzite, amethyst, diamond, glass, lead-quartz, or any otherwise similar naturally occurring, lab grown, man-made, extra-terrestrial, artificial, or synthetic crystal. Any gem or crystal can be used similarly as a 'host crystal', though there are more scientific properties to some 'host crystals', and some 'host crystals' are used for their aesthetic properties. The details of, and a great matter of the scientific nature of this invention is in the natures of quartz, calcite, tourmaline, and other piezoelectric gems, crystals, and mineral combinations. Examples of the shapes and sizes that are used in this invention as the 'host crystal' include but are not limited to; crystals designed for jewelry, pendants, decorative carvings, natural uncut specimens, crystal art, massage wands, crystal wands, pyramids, geometric or non-geometric shapes, points, doughnut shapes, spheres, egg shaped, "Vogel (cut) crystals", double terminated-"D.T. crystals", "Pranic crystals", and single terminated "S.T." crystals. We have represented many of these common shapes of crystals which are used as the 'host crystals' in/of this invention on Page 1 and throughout the drawings of this application.

All shapes, sizes, styles, colors, and designs of 'host crystals' are used in largely the same way in this invention. 'Host' crystals are first drilled, then they are filled and compressed with minerals and other materials stated, these materials are then capped into the 'host crystal' with metals. As an option for further magnetism and compression of the 'host crystal', the 'host crystal' of this invention can be further compressed and magnetized using neodymium, samarium cobalt, ferrous, or electromagnets.

The most specified and intensive full use of our invention will be used on jewelry, decorative specimens, and with 'Pranic' and 'Vogel' crystals which are used in energy, homeopathic, magnetic, and light therapy applications, but the same basic processes described are used in all sizes, shapes, designs, and types of 'host crystals' in this invention.

Page 1 of the Drawings shows many of the common quartz crystal shapes that are used as 'host crystals'; all the shapes represented are to be used in relatively the same ways in this invention. (Page 2 FIG. 1) shows Vogel and Pranic crystals, double and single terminated 'host crystals'.

Describing this invention further. This patent application describes, and is for, the drilling into a piece of any quartz, or any similar 'host crystal', then filling that drilled hole with gems/crystals, and any combination of any minerals, any metals (besides solid gold rods described of the prior art), any magnets, any materials deemed beneficial by health care therapists, any items of intrinsic value including; plant materials, any organic materials, any homeopathic remedies, any vitamin(s), any legal and unpatented prescription or non prescription drug(s), any herbal medicines/remedies, any (beneficial) bacteria, beneficial cells such as spirullina, any (beneficial) microbes, homeopathic or structured waters, homeopathic remedies, plant essences, any monatomic metals, any Ormus, any items of special significance to an individual such as animal remains or souvenir, synthetic remedies/medicines to the inside of a quartz, calcite, topaz, diamond, tourmaline, ruby, selenite, amethyst, morganite, kunzite, moldavite, or similar crystal. Any of these types of crystals may be used in the same ways, as the 'host crystal' in this invention.

The (bare) Crystal shapes represented on page 1 of the drawings of this in this application, are examples of 'host crystals'. The 'host crystals' are first drilled to any depth desirable in any spot on the 'host crystal' that is desirable. As stated prior, that hole is then filled with a chosen combination of ant these afore mentioned minerals, metals, organic and inorganic materials. Then this mix of ingredients is packed into and forcefully compressed into the hole(s) that is drilled into the 'host crystal'. All shapes of quartz or similar crystal work relatively the same ways, using the same materials and techniques in this invention. The crystal is drilled, penetrating through the surface of the crystal to varying depths. The depth drilled depends on the size, style, and application of the crystal. This hole that is drilled into the crystal is filled/packed with gemstones, minerals, metals, herbs, plants, and homeopathic remedies. These fillings are compressed into the hole that is drilled into the crystal; this hole was specifically drilled for the purpose of filling it with said materials stated of this invention. This compression should be done to the greatest extent of pressure possible without breaking the 'host crystal' in which the fill is being placed/compressed.

Examples of gems, minerals, and metals used to fill the drilled hole(s) in the 'host crystal' of this invention are, but are not limited to; ruby, amethyst, emerald, kunzite, jasper, morganite, topaz, garnet, rose quartz, smoky quartz, lodestone, citrine, meteorite, sapphire, moldavite, malachite, tourmaline, hematite, loadstone, shunghite, fulgerite, turquoise, diamond, gold, silver, platinum, palladium, copper, brass, tin, iron, etc. etc. There is no limit to the variety of different gems, minerals, and metals, organic and inorganic materials that can be added to the 'host crystal(s)'. Combinations of these materials and others listed prior, can be crushed, flaked, mashed, disintegrated, cut, ground, or powdered into a desired size, then they are compressed into the hole(s) that is/are drilled into the 'host crystal'.

Further describing the holes drilled into the 'host crystals'. These holes are represented in the drawings on (Page 2 as FIG. 3), (Page 3 as FIG. 13), and (Page 4 as FIG. 2) of this application. These figures represent the holes that are drilled into the quartz, calcite, or similar 'host crystal'. The 'host crystal' is drilled, penetrating a desired/necessary hole. The drawings show the hole to penetrate into and through a portion of, or penetrating all of the way through the 'host crystal'. To re-state this notion: the drilled holes can fully penetrate the crystal from one side, and through to the other side, or the holes can be drilled to penetrate only a percentage or portion of the way through the crystal (Page 2, FIG. 3). The hole that is drilled into the 'host crystal' is a hole that can range from less than 1 mm, to over 8+ centimeters in diameter. The diameter of the hole will depend on the desired application and the size of the 'host crystal'. The hole(s) in the 'host crystal' vary in depth, widths (diameter), as well as in the number/amount of holes that are drilled into the 'host crystal'. Naturally formed holes, pockets, or fractures in crystals can be filled with this same process. This patent application is not for the drilling or creation of a hole inside of a 'host crystal', but it is for the filling and capping of holes into 'host crystals' that are drilled, created, or naturally occurring. The hole(s) are drilled into the 'host crystal' with a diamond or carbide tipped drill-bit, and may also be accomplished by laser penetration. The hole diameter and depth will vary depending on size and shape of the 'host crystal'. The desired filling and application of the 'host crystal' can also determine size, placement, and depth of the holes. The holes can be on the anywhere on the 'host crystal.' The holes can be anywhere on the bottom, top, sides, or anywhere else on the 'host crystal', as is represented in the drawings. The drawings show options for the placements of the hole(s) that are drilled into the 'host crystals'. There is no minimum or limit to the size or number of holes in the 'host crystal'. The actual placement of, number of, or Size(s) of the hole(s) is completely relative to the application and to scale/dimensions of the actual 'host crystal'. The drawings are only examples of potential placements, depths, and sizes. The hole(s) are filled with the afore mentioned combinations of gem, minerals, metals, magnet, plant, organic, inorganic, herb-homeopathic materials etc. and are capped by pressing/mashing metal flake or powder, usually silver or gold, semi-permanently capping and compressing the minerals, gems and other ingredients inside of the hole drilled into the 'host crystal'.

Capping the 'Host Crystal':

(Page 2, FIG. 2), (Page 3, FIG. 1), and (Page 4, FIG. 1) of the drawings show a circle or oval, represent the metallic cap that semi-permanently covers/caps the filled hole in the 'host crystal' of this invention. This cap is made of a metal flake or powder that has been pressed/mashed onto the top of the materials that fill the hole in/of the 'host crystal. The pressing of this metal flake can be done by hand with a push-rod, or with a vise or machine press. The object is to get the flake material to form, through the compression, into a solid metal cap. These metallic caps effectively, aesthetically, and semi-permanently covers, caps, and further compresses the minerals and other ingredients that fill the hole into the 'host crystals'.

The holes in the 'host crystal', as shown on Page 2 as FIG. 2, Page 3 as FIG. 1, Page 4 as FIG. 1, and the tunnels into the 'host crystal' as shown on Page 2, FIG. 3, Page 3, FIG. 13, and Page 4, FIG. 2, are used in this invention to fill a 'host crystal' with gems, minerals, homeopathies/plants materials, herbs, vitamins, medicines, and magnetically conductive metals and other materials afore mentioned. These materials are usually crushed, ground, pulverized, cut, or otherwise made into a desired sized fill material. Materials that will fill the holes will range from very large materials for very large holes, to grain or to powder sized material. The materials can be of any shape as long as they fit into the hole/recession made into the 'host crystal'. The size of the materials that are embedded into the recession/hole of the 'host crystal' depends on the size of the hole/depression that exists or is created into/within 'host crystal' that is to be filled with these materials. Next, the material is placed into the drilled hole and compressed into that hole in the 'host crystal'. These materials are mashed and compressed into the hole in the 'host crystal'. These materials to varying degrees into the inside of the 'host crystal', but are usually filled into the 'host crystal' until they are nearly to the top of the hole in the 'host crystal'. The materials are usually filled into the 'host crystal's' hole until they come within ½ to 3 mm from the top. The ½ to 3 millimeters is left as an area and room to for the metallic flake that will form the cap. This ½ to 3 mm are is then filled with gold, silver or other metallic flake and mashed into forming the hole's metallic cap. The mashing/compression of the metal flake onto the materials that are filled into the hole that was drilled into the 'host crystal' effectively causes further compression within the 'host crystal'. The metals most commonly used to cap the hole in the 'host crystal' are gold, silver, platinum, palladium, and copper, but any and all metal flakes and powders can be used in largely the same way in this invention to effectively cap the materials inside of the crystal. There is no other invention, jewelry, therapy, or tool that uses metal molded onto gems or crystals in this way.

This part of the invention describes the combination of magnetism (magnets) onto and/or into the 'host crystal'.

Figure 4:
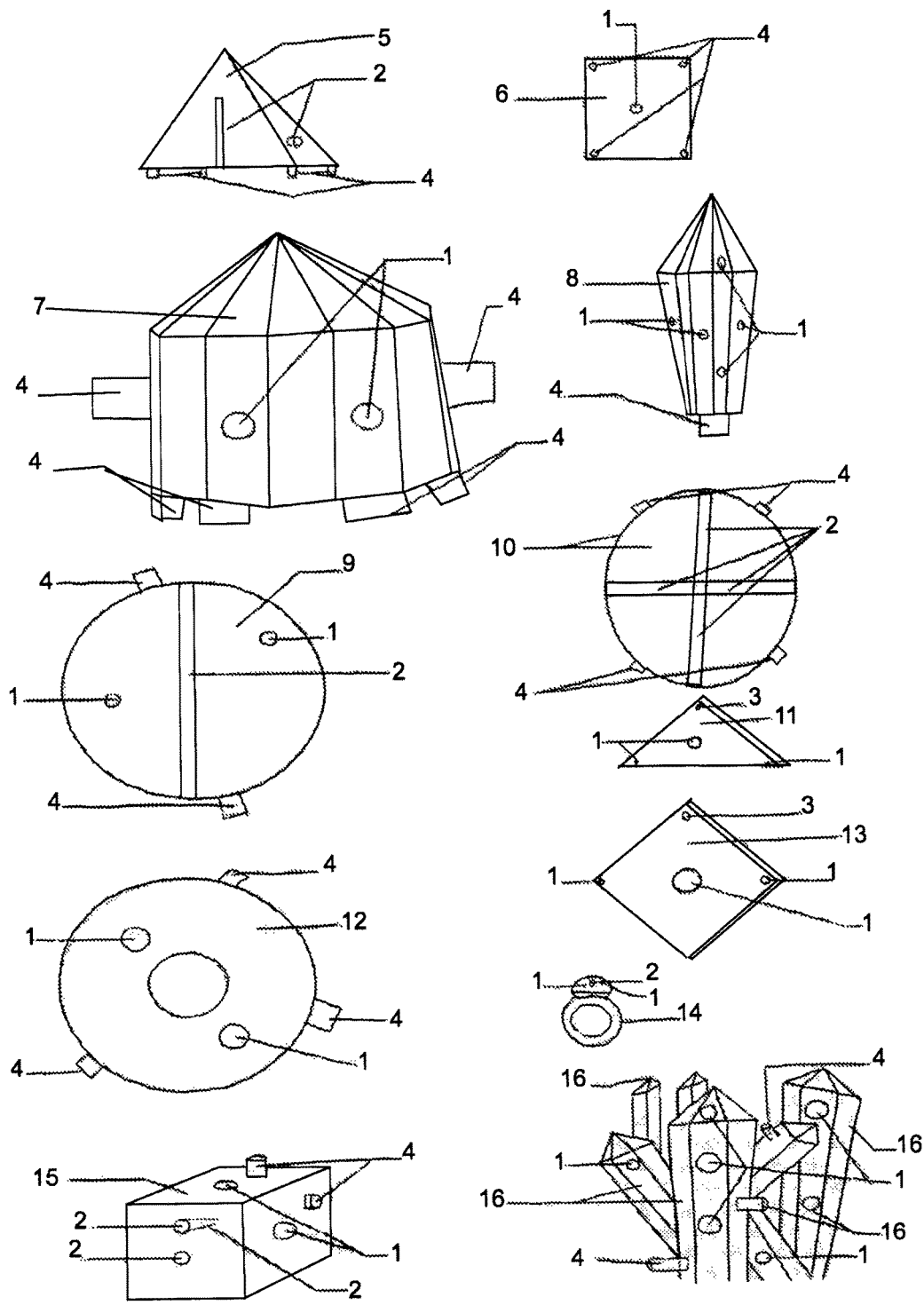

These magnets are represented in the drawings on Page 2, FIG. 4, Page 3, FIG. 2, and Page 4, FIG. 4.

Magnets can be added by to the 'host crystal' by gluing them with epoxy or other glues, or otherwise bonding them to the surface or surfaces of the 'host crystal'. The magnets of this invention can also be added into a hole drilled into the crystal, a hole that is drilled specifically into the 'host crystal' for the purpose of fitting and/or recessing a magnet(s) into the crystal. Then magnets can be placed, glued, packed, or otherwise compressed into a hole drilled into the 'host crystal'. These holes for the magnets, and all holes placed into the crystals of this invention can be capped into the crystal by epoxy, melted glass, or by pressing metal flake onto it the top of it, or otherwise effectively capping, compressing, and sealing the magnets and other materials into the crystal.

The magnets used in this invention are usually disk shaped 'rare Earth' magnets, or ferrous magnets, but can be any form, type, size, shape or strength of magnets. These are glued or otherwise bonded onto the surface of the 'host crystal', or set (recessed) into the 'host crystal', then the magnet(s) would be bonded into the hole or capped into it with metal, epoxy, cement, or other similar means of permanently or semi-permanently attaching the recessed magnet(s) into 'host crystal'. The magnets are set onto or into the 'host crystal' in an array in order to create a magnetic torsion field of attractions and repulsions onto and into the 'host crystal'. A magnetic field is also established inside of the 'host crystal' utilizing only a single magnet that is attracted to magnetically conductive materials that are filled into 1 or more holes inside of a 'host crystal'. The magnets used in this invention vary in strengths (gauss ratings), types, coatings, shape, and size. Magnets are placed anywhere on the surface of, or anywhere within the 'host crystal'. The magnets are arranged on and within a 'host crystal' in a way that they interact with each other magnetically, and/or with the magnetically conductive minerals and metals that are compressed into, and capped inside of the 'host crystal'.

Other forms of magnetism may be used including DC electro magnetism. The notion of the magnets of this patent is to drive/induce a magnetic compression to the crystal by squeezing the crystal between 1 or more magnets, and the magnets interaction with the materials inside of the 'host crystal'. The magnets effectively and continually compress the crystal, as well as magnetically charge (magnetize) the loadstone, hematite, iron and other magnetically conductive materials placed inside 'host crystal'.

The advantage of the present invention includes, without limitation; it is a combination of therapy tools of various alternative medicine practitioners and holistic health-care practices. It is a magnetic mineral and homeopathic therapy tool utilizing magnetic and magnetized minerals, that act as a means to buffer and cohere magnetic enhancements, magnetic field therapies, and light therapies.

Adding magnets to the inside of quartz and other materials making the 'host crystal' allows for the buffering of the very strong energy field of the neodymium or samarium cobalt therapy magnets.

This invention is a way to provide a complete gem-mineral, vibrational-energy, and homeopathic energy enhancement tool. Practitioners of 'energy medicine' are using these types of materials often, yet separately. Examples of these are Reiki, Pranic, Quantum touch, and other 'bio-energy healing' therapies. This invention combines the gems, crystals, magnets, and other energetic materials that they use in their vibrational and bio-energy treatments.

This is a tool of Negative Ion Generation. Certain materials used within and of this invention such as quartz, generate negative ions. Through this way of combining and compressing the materials as in this invention, the negative ion generation of certain materials is greatly amplified/increased over the negative ion generation of the materials used separately. This is known as a very beneficial step and result of the procedures and materials of this invention.

This invention also effectively combines quartz with gem, mineral, magnetism, and light creating a magnetic gem and mineral light therapy that can effectively combine infinite arrangements and combinations of different gem and mineral species. This gives practioners of light therapies a new and infinite variety of optical effects to provide to their clients. Other Gem Light therapies only involve up to 12 different gems with not magnetism present in those therapies.

Before this invention, light, magnetic, gem, mineral, and homeopathic therapies and enhancements have all been largely separate therapies practiced by separate therapists. This invention also serves as a way of effectively inducing light and magnetism into and through quartz, gems, and the other materials listed in this application. Many of the same holistic, and many traditional health therapists see and are experiencing this as having an improved therapeutic effect than do light or magnetic therapies alone. Practitioners of traditional, holistic, homeopathic, magnetic, and vibrational/energy therapies understand this invention as a potentially therapeutic combination of tools that have been long used.

The gem, mineral, homeopathic, organic and non-organic material filled crystals described in this application, also effectively combine existing forms of light and laser therapies, with the materials of the crystal of this invention. This is the first therapy of its kind. This invention will also combine these 'gem-mineral light therapies' with the magnetic therapy potentials of this device.

This is a homeopathic, magnetic, and in gem/mineral cohered light therapy. These crystals can be cut to a style that fits a light fixture, filled with gem materials as described in this patent, and mounted to that light fixture. Then lights or lasers are shone through the 'host crystal' that is filled with gems, minerals, and other ingredients inside of it. Then this light and magnetism is focused onto a person or animal's body receiving this 'magnetic gem, mineral, and homeopathic light therapy.'

This invention will also effectively and aesthetically combine gems, crystals, minerals, metals, and homeopathic materials, with magnetic therapy in the form of decorative specimens and for jewelry. These jewelry or magnetic therapy devices are worn on the body to induce the subtle energy/vibrations of the crystals, minerals, homeopathic materials, and the magnetism involved in this invention into the body. This is seen to be beneficial to the blood of the body, the 'Aura energy field' of the body. It is a way to aesthetically combine monetarily valuable materials with those deemed special, sentimental, or even sacred to an individual. The crystals, gems, precious metals and other materials involved in this invention are seen as a very aesthetic, valuable, and energetic way of combining a person's favorite gems and precious metals of jewelry, with holistic energy (magnetic) and homeopathic/vibrational therapy materials, along with other sentimental objects that are all combined functionally, therapeutically, and aesthetically.

It is a way to combine an infinite variety of gems and homeopathic materials to be worn as adornment, or used as energy enhancement/therapies.

What we claim as our invention is:

1. A filled crystal, comprising:
   a host crystal possessing at least one cavity, wherein said cavity is filled with material inserted into said cavity under compression; and
   a seal for retaining said material within said cavity under compression.

2. The filled crystal of claim 1, wherein said seal comprises metal particles that are compressed along with said material so as to form a solid metallic plug.

3. The filled crystal of claim 2, wherein said host crystal comprises a crystal made of one of quartz, calcite, topaz, ruby, sapphire, diamond, or tourmaline.

4. The filled crystal of claim 1, further comprising one or more magnets affixed to said host crystal.

5. The filled crystal of claim 4, wherein said material is capable of enhancing the magnetic field of said one or more magnets.

6. The filled crystal of claim 4, wherein said one or more magnets are affixed to said host crystal by placing said one or more magnets within one or more additional cavities.

7. The filled crystal of claim 4, wherein said one or more magnets are positioned so as to allow the fields of said one or more magnets to interact with the material.

8. A filled crystal, comprising:
   a host crystal possessing a plurality of cavities, wherein at least one of said plurality of cavities is filled with at least one type of material inserted into said cavity under pressure; and
   at least one seal for retaining said material into said plurality of cavities whereby said materials are maintained under pressure.

9. The filled crystal of claim 8, wherein said seals for retaining said material are comprised of metallic particles that are compressed so as to form solid metallic plugs.

10. The filled crystal of claim 8, further comprising one or more magnets affixed to said host crystal.

11. The filled crystal of claim 10, wherein said one or more magnets are affixed to said host crystal by inserting said one or more magnets into at least one of said plurality of cavities.

12. The filled crystal of claim 10, wherein said one or more magnets are affixed to said host crystal in an arrangement that allows the magnetic field of said one or more magnets to interact with said material.

13. The filled crystal of claim 12, wherein said material possesses magnetic properties.

14. A method for creating a filled crystal, comprising:
   creating at least one cavity in a host crystal;
   filling said cavity in said host crystal with material;
   compressing said material within said cavity; and
   sealing said cavity.

15. The method of claim 14, wherein said sealing of said cavity is accomplished by compressing metallic particles so as to form a solid metal plug.

16. The method of claim 14, further comprising permanently affixing one or more magnets onto said host crystal.

17. The method of claim 16, wherein said permanently affixing said one or more magnets onto said host crystal comprises:
   creating at least one additional cavity in said host crystal;
   inserting said one or more magnets into said at least one additional cavity; and
   sealing said one or more magnets into said at least one additional cavity.

18. The method of claim 17, wherein said creating and inserting steps are performed so as to result in said one or more magnets being arranged so as to allow said magnets' fields to interact with said material.

* * * * *